(12) United States Patent
Srinivasan (10) Patent No.: US 6,612,150 B2
(45) Date of Patent: Sep. 2, 2003

(54) METHOD AND DEVICE FOR MEASURING ABRASIVE PROPERTIES OF PAPER AND OTHER SHEET MATERIALS

(75) Inventor: Raghavan Srinivasan, Beavercreek, OH (US)

(73) Assignee: Wright State University, Dayton, OH (US)

( * ) Notice: Subject to any disclaimer, the term of this patent is extended or adjusted under 35 U.S.C. 154(b) by 0 days.

(21) Appl. No.: 10/091,828

(22) Filed: Mar. 6, 2002

(65) Prior Publication Data

US 2002/0194894 A1 Dec. 26, 2002

Related U.S. Application Data (60) Provisional application No. 60/273,915, filed on Mar. 7, 2001.

(51) Int. Cl.[7] .................................................. G01N 3/56
(52) U.S. Cl. ........................................................ 73/7; 73/81
(58) Field of Search .................................. 73/7, 81, 159

(56) References Cited

U.S. PATENT DOCUMENTS

| | | | |
|---|---|---|---|
| 3,554,007 A | | 1/1971 | Hu |
| 3,827,281 A | | 8/1974 | Hamel |
| 3,979,951 A | * | 9/1976 | Munden et al. ............... 73/159 |
| 4,253,913 A | | 3/1981 | Chaudhuri |
| 4,633,701 A | | 1/1987 | Einlehner |
| 4,864,852 A | * | 9/1989 | Boone .......................... 73/159 |
| 4,928,533 A | | 5/1990 | Bachelder et al. |
| 5,542,281 A | | 8/1996 | Lee et al. |
| 6,142,010 A | * | 11/2000 | Merck, Jr. et al. ............... 73/81 |

OTHER PUBLICATIONS

R. Srinivasan et al., "A New Method for Testing the Abrasive Properties of Paper and Other Sheet Materials" Journal of Testing and Evaluation, American Society for Testing and Materials, 2001, pp. 72–78.

* cited by examiner

*Primary Examiner*—Hezron D Williams
*Assistant Examiner*—Charles Garber
(74) *Attorney, Agent, or Firm*—Killworth, Gottman, Hagan & Schaeff, L.L.P.

(57) ABSTRACT

The present invention provides a device for testing the abrasiveness of paper and other sheet materials. The device comprises a punching module, a feed module for moving the material, a holding module that holds the material while the punching module penetrated the material, and an instrument that records and analyzes the amount of force needed to punch through the material and then calculates the abrasive properties of the material. The punching module comprises a punching instrument for punching the material, a driving mechanism for operating the punching instrument, and a measurement system that measures the amount of the force required to punch the material. A method for using the device is also provided.

40 Claims, 8 Drawing Sheets

METHOD AND DEVICE FOR MEASURING ABRASIVE PROPERTIES OF PAPER AND OTHER SHEET MATERIALS

CROSS-REFERENCE TO RELATED APPLICATIONS

This application claims the benefit of U.S. Provisional Application Serial No. 60/273,915, filed Mar. 7, 2001.

BACKGROUND OF THE INVENTION

The present invention relates to an abrasiveness test for paper and other sheet materials. More specifically, the present invention relates to a method and device for measuring the abrasiveness of paper and other sheet materials by measuring the change in force required to punch the material.

Several different abrasion tests have been proposed and are currently in use for testing the abrasion resistance of paper. For example, there is a mechanical "wet thumb" test which rubs the surface of the paper, giving the wet abrasion resistance of the paper and a numerical evaluation of the wet abrasion resistance of the paper. This test is particularly important in relation to papers such as blueprint, cartographic papers, or any paper that is handled and used while wet.

Another abrasion test for paper is the Taber Abraser, which is used for testing both wet and dry paper. This apparatus uses a horizontal motor driven turntable to which the specimen is attached and a special wheel with embedded abrasive particles that rotate on the specimen. The abraded material is removed by suction and is weighed. The weight of the abraded material, called "Abrasion Loss" is a measure of the abrasion characteristics of the paper.

Another test draws an eraser over the surface of the paper and measures the number of passes necessary to wear a hole. This is particularly important for writing papers that must tolerate erasures without impairing the surface characteristics.

The Bekk Test is used to predict the wear imparted to printing surfaces by heavily loaded papers (papers with very high filler content) or papers that liberate mineral dust, when in use. This test measures abrasion by drawing a strip of paper through a distance of 10 cm between a glass plate and a rotating roller which hold the paper in contact with the glass at a pressure of 1 kg/sq. cm. of width of strip. Very fine scratches produced on the surface of the glass are counted and measured under a microscope. The results obtained are used to predict the wear characteristics of the paper on printing plates.

The knife-edge abrasion test, as taught in U.S. Pat. No. 3,827,281 to Hamel, is used to measure the abrasiveness of paper (and other sheet materials) by pressing a sharp but relatively easily dulled cutting edge onto a stack of paper. The pressure necessary to move the knife-edge through the layers relative to the depth of cut indicates the dulling of the knife. The abrasion characteristics of the paper are then calculated in relation to the rate of the dulling of the knife.

By far, the most widely used test for measuring dry abrasion due to paper is the needle penetration test or the sewing machine test developed by the Institute of Paper Chemistry (IPC) needle penetration test. This method involves puncturing a paper sample with a standardized bronze needle mounted on a sewing machine. The loss in weight of the needle after many (10,000 to 50,000) penetrations is used as a measure of the abrasive characteristics of the paper. This method has proved to be reliable for predicting the life of guillotine trimmer knives, and is sensitive enough to detect the effect of various additives and substrates.

The needle penetration test, however, has serious drawbacks. First, the weight loss during a test may range between 0 and about 1000 $\mu$g, with 100 $\mu$g being typical. With such a small change in weight, preparation and handling of the needle become critical, since small changes in weight can be introduced during handling or from paper debris. Second, the size of the paper sample to make 50,000 punches is considerable, and the test itself is time consuming. All these factors restrict the use of the needle penetration test to a clean laboratory.

Accordingly, there is still a need for a method and device for measuring the abrasiveness of paper and other sheet materials that is more accurate, more efficient and uses less material.

SUMMARY OF THE INVENTION

The present invention meets those needs by providing a device and a method for testing the abrasiveness of paper and other sheet materials that is less sensitive to operator error and environmental conditions and uses less material. The method uses the force required to punch through a material as the basis in determining the abrasiveness of the material, thereby alleviating the need to weigh the punching instrument and the need to calculate the rate of dulling of the punching instrument. The device maintains a continuous record of the force required to make a single punch in the material and maintains a continuous record of the unremitted force required to make a series of punches in the material. The record is then analyzed and the abrasiveness of the material is determined.

In accordance with one embodiment of the invention, a device for measuring abrasive properties of a material is provided comprising a punching module; a feed module for moving the material in relation to the punching module; a holding module that holds the material while the punching instrument penetrates the material, having a first position and a second position that couples to the feed module; and an instrument that records and analyzes the amount of the force needed to penetrate the material and calculates the abrasive properties of the material. The punching module comprises a punching instrument for punching the material, a driving mechanism for operating the punching instrument, and a measurement system that measures the amount of the force required to punch the material.

In accordance with another embodiment of the invention, a method for measuring abrasive properties of a material is provided comprising placing the material on a feed module, feeding the material relative to a punching module, holding the material stationary with a holding module, punching a material with the punching tool, measuring the amount of force necessary for the punching tool to punch the material, storing the force measurement for the punching tool to pierce the material, recording the force measurement that is stored, analyzing the force measurement, and determining the abrasiveness of the material.

Accordingly it is a feature of the invention to provide a device and method for measuring the abrasiveness of a material by measuring the amount of force necessary to punch a material. It is another feature of the invention to provide a device and method for measuring the abrasiveness of a material by measuring the amount of unremitted force necessary to make a series of punches in a material. Other features and advantages of the invention will be apparent from the following description, the accompanying drawings, and the appended claims.

DETAILED DESCRIPTION

The invention is best described by referring to the Figures. Referring to FIGS. 1–4, a device 10 for measuring the abrasive properties of a material 14 is provided. The material can be paper, sheet metal, foil, plastic sheet, plastic foil, woven fabric, non-woven fabric, or any sheet products that are subject to cutting, slitting or perforating.

Figure 1:
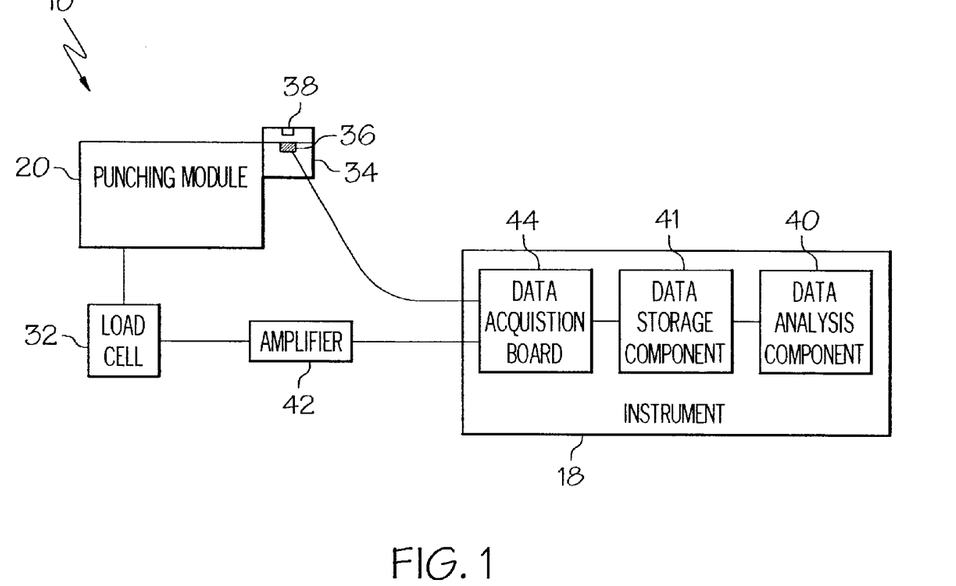
FIG. 1 is a schematic diagram of one embodiment of the present invention.
Figure 2:
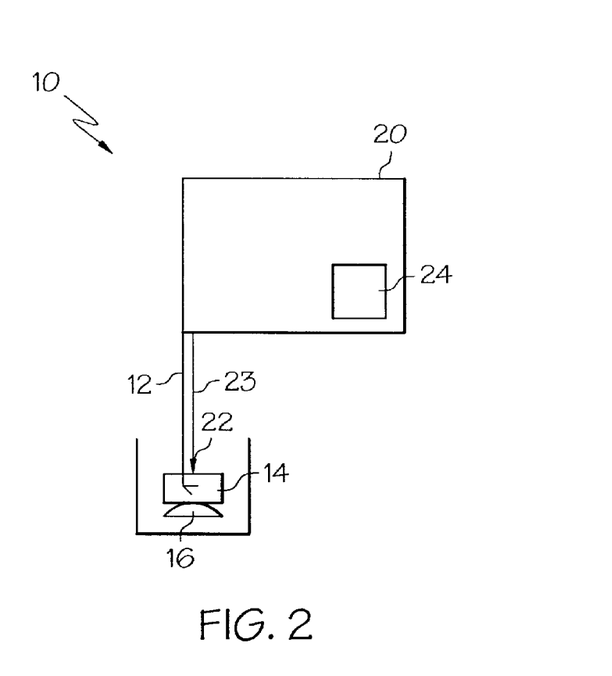
FIG. 2 is a schematic diagram of the punching module, the feed module, and the holding module of the present invention.

The device 10 comprises a punching module 20, a holding module 12, a feed module 16, and an instrument 18 that records and analyzes the data. The punching module 20 comprises a punching instrument 22, a driving mechanism 24, and a measurement system 30. The punching instrument 22 is generally coupled to a punching member 23 that extends from the punching module 20. The punching member 23 allows the punching instrument 22 to move in a first direction and a second direction in order to punch through the material 14. The punching instrument 22 can be blunt or pointed and is preferably made of a sturdy material. Typically, the punching instrument 22 is a needle. The tip geometry and the material for the punching instrument 22 are preferably selected in such a way that the punching instrument 22 is sufficiently sturdy so as not to bend while punching through the material 14, but should wear due to the abrasiveness of the material 14. The driving mechanism 24 operates the punching member 23. The driving mechanism can be a motor or any other device that will activate the punching member 23.

Figure 3:
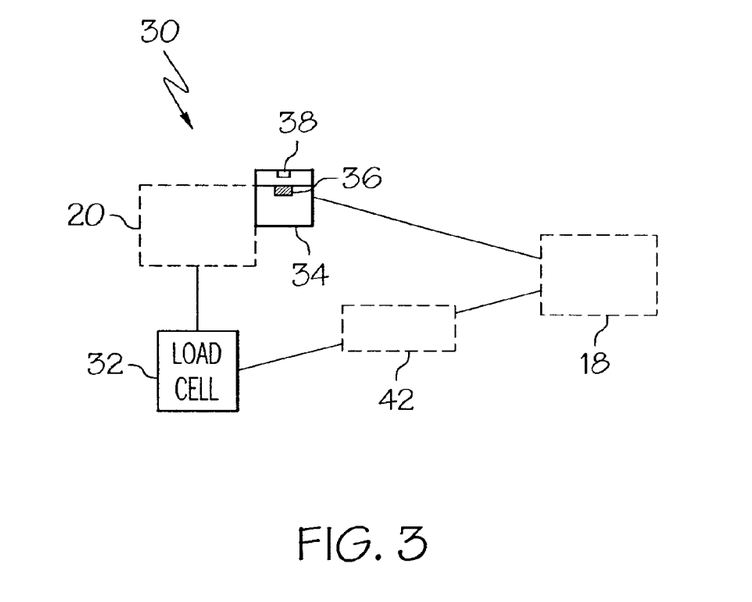
FIG. 3 is a schematic diagram of the measuring system.
Figure 4:
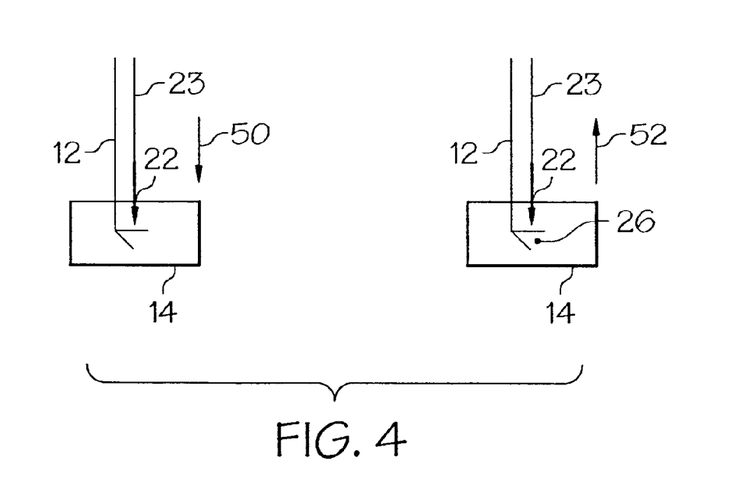
FIG. 4 is a schematic diagram of the punching instrument performing compressive force and tensile force.

The measurement system 30 comprises a load cell 32 and a sensor mechanism 34. The load cell 32 is an electrically operated device, such as a piezoelectric device with 10 lbs capacity and an output of 0.5 V/lb with a 0.02% sensitivity of full scale. Force measuring systems of greater or lesser capacity and sensitivity, such as a strain-gauge load cell, may be used depending on the nature of the material being tested in place of the piezoelectric load cell. In that case, a negative voltage signal will be indicated when the force is compressive and a positive voltage signal when the force is tensile. The load cell 32 provides a positive output signal and a negative output signal according to the type of force being applied to the load cell 32. The two primary forces applied to the load cell 32 are compressive force 50 and tensile force 52. The load cell 32 gives a positive output signal when compressive force 50 is being applied to the load cell 32 and a negative output signal when tensile force 52 is being applied.

The sensor mechanism 34 detects the compressive force output signals from the load cell 32. The sensor mechanism 34 comprises a movement tracking device 38 and a sensor 36. The movement tracking device 38 is coupled to the drive mechanism 24 in a manner that allows the movement of the movement tracking device 38 to be associated with the movement of the drive mechanism 24. Therefore, when the drive mechanism 24 activates the punching member 23 to apply compressive force to the material 14, the movement tracking device 38 also moves. The sensor 36 is typically an infrared sensor that detects the movement of the movement tracking device 38.

The holding module 12 holds the material 14 firmly in position while the punching instrument 22 punches the material 14. Typically, the holding module 12 is a clamp. The holding module 12 can be placed in a first position or a second position. When the holding module 12 is in the first position, it is not coupled to the material 14, thus the material 14 can be easily removed from the device 10. When the holding module 12 is placed in the second position, the holding module 12 is coupled to the material 14 and holds the material 14 in position. However, the material 14 can move with the feed module 16 and be punched by the punching instrument 22 in either the first position or second position.

The feed module 16 moves the material 14 through the punching module 20. After the material 14 has been punched, the feeding module 16 moves the material 14 further along the device 10.

The instrument 18 records and analyzes the force data sent by the measuring system 30 and calculates the abrasiveness of the material 14. The instrument 18 is typically a microcomputer comprising a data acquisition board 44, a data storage instrument 41, and a data analysis instrument 40. The data acquisition board 44 is converts the signal from the sensor 36 and the load cell 32 so that the instrument 18 can read the force data. The data storage instrument 41 stores and records the peak punching force as well as the unremitted force. By peak punching force, it is meant that the highest amount of force necessary to punch the material 14. The data analysis instrument 18, analyzes the data and the abrasiveness of the material 14 is then calculated from the force data that is collected. The instrument 18 is linked to the punching module. Typically, the instrument 18 is electrically linked to the punching module, however, the instrument 18 can be linked in any manner that allows the instrument to record the force used to punch the material 14.

During a typical punching cycle, the material 14 is placed in the feed module 16 and the holding module 12 is in the second position to secure the material 14. The punching instrument 22 is driven through the material 14. Then the punching instrument 22 is pulled out of the punched hole 26. The feed module 16 then moves the material 14 in order to receive another punch.

The force used to drive the punching instrument 22 through the material 14 is compressive force 50. The force used as the punching instrument 22 is pulled out of the punched hole 26 is tensile force 52. For purposes of this embodiment, only compressive force 50 results are needed. Therefore, a sensor mechanism 34 is incorporated into the device 10. The sensor 36 detects the movement of the movement tracking device 38 and alerts the instrument 18 just prior to the punching instrument 22 making contact with the material 14 that a compressive force 50 will be applied against the load cell 32.

Figure 5:
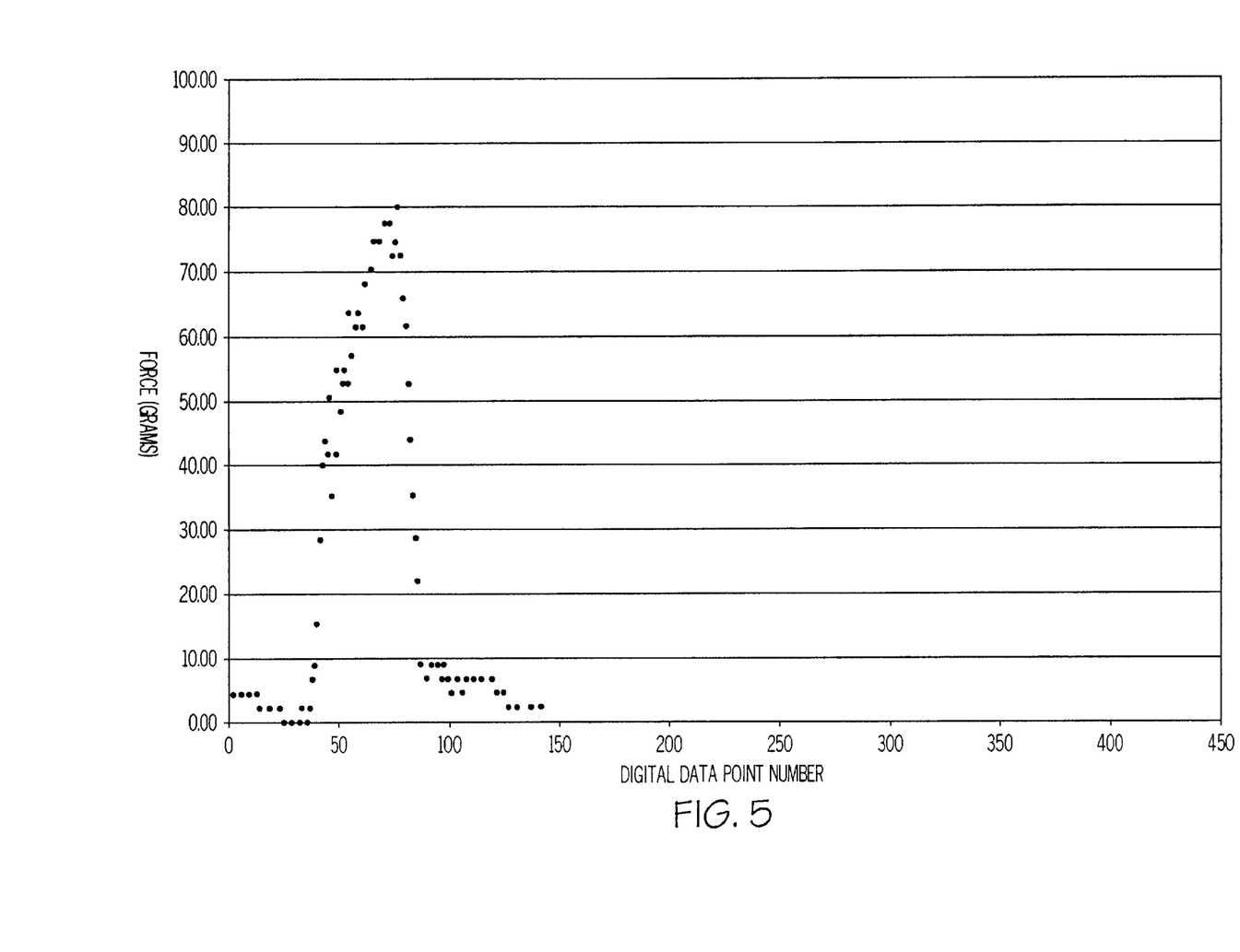
FIG. 5 is a graph of compressive force for a single punch.
Figure 6:
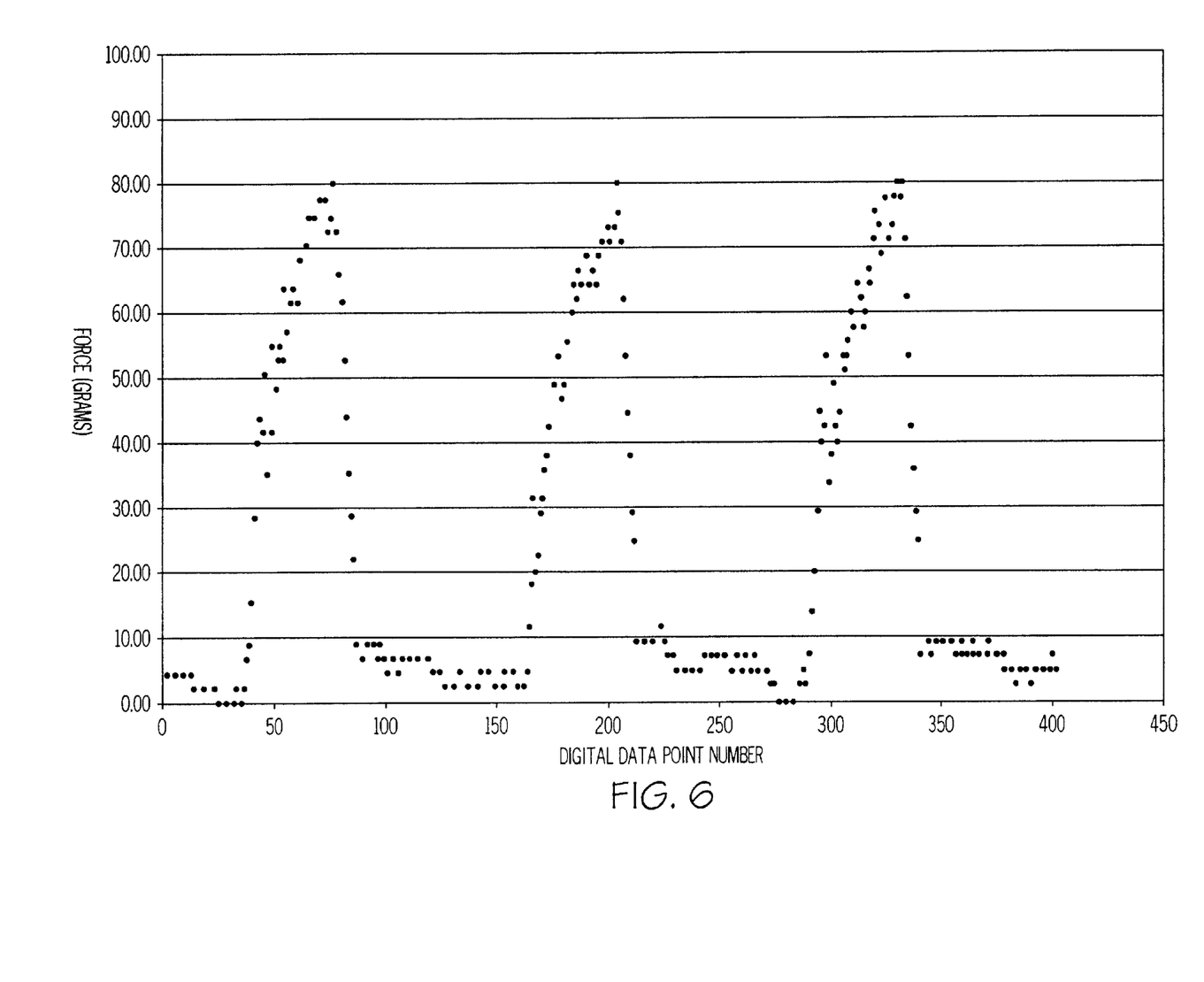
FIG. 6 is a graph of unremitted compressive force.
Figure 7:
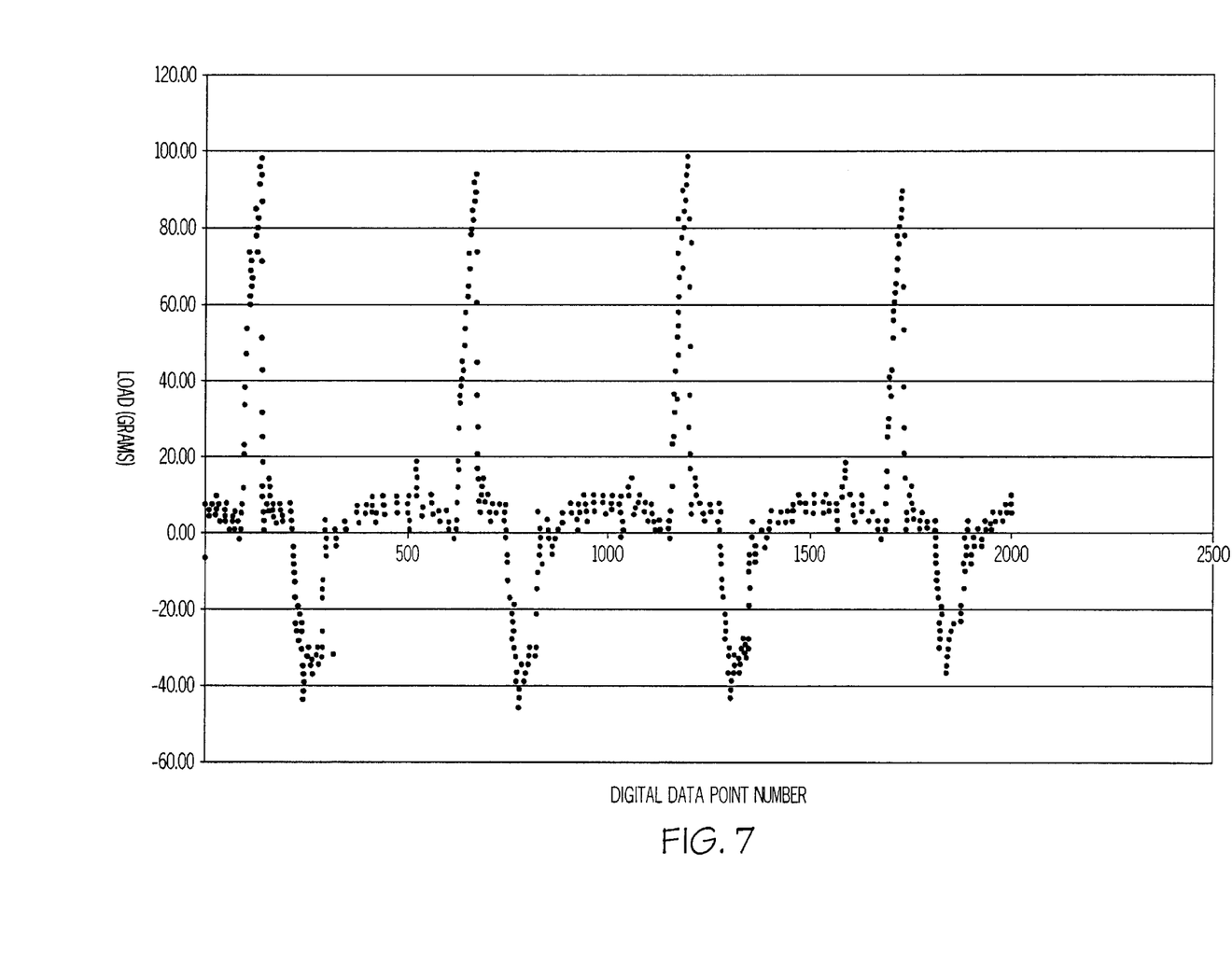
FIG. 7 is a graph of compressive and tensile force.

The signal from the sensor 36 and the signal from the load cell 32 are sent to the data acquisition board 44. The data acquisition board 44 converts the analog signals from the sensor 36 and the load cell 32 into digital signals. The instrument 18 reads both the digitized signal from the load cell 32 and the digitized signal from the sensor 36. The instrument 18 only records and stores the data from the load cell 32 when the instrument 18 reads a signal from the sensor 36. Thus, as shown in FIGS. 5 and 6, only the compressive force 50 of the punching instrument 22 against the load cell 32 is recorded. Without the use of the sensor 36, the instrument 18 would record and store both the tensile force 52 and the compressive 50, as shown in FIG. 7. The signal from the load cell 32 may have to be directed to an amplifier 42 before reaching the instrument 18.

The measuring system 30 continues to measure the amount of force used to make the punches in the material 14 and does not stop measuring the amount of force until the punching member 23 ceases punching the material 14. Therefore, the instrument 18 continues to record and store the force data received from the measuring system 30 until the measuring system 30 stops sending force data. Thus, the instrument 18 maintains a continuous record of the force that is required to punch the material 14. The force is the force that is continually pressed against the material for one punch, as shown in FIG. 5. Referring to FIG. 6, the instrument 18 can also maintain a continuous record of the unremitted force over a series of punches. More specifically, the force applied to the material 14 is not stopped or interrupted over a period of time, thus allowing for the punching member 23 to make a series of punches in the material 14. The instrument 18 then analyzes the force data and calculates the abrasivity of the material 14.

The method and apparatus are effective in distinguishing between various materials based on using the slope of the trend line of punching force as a measure of abrasivity. This method and apparatus are sufficiently sensitive to pick up differences resulting from different material-making parameters. The method and apparatus therefore have the potential to meet the needs of both converters, for identification of materials that are most abrasive and likely to damage manufacturing equipment, and manufacturers, for measuring the effect of the material-making parameters on the properties of the material that they produce.

The invention will be further described by way of examples, which are intended to be illustrative of the invention, but not limiting in scope.

EXAMPLE 1

Figure 8:
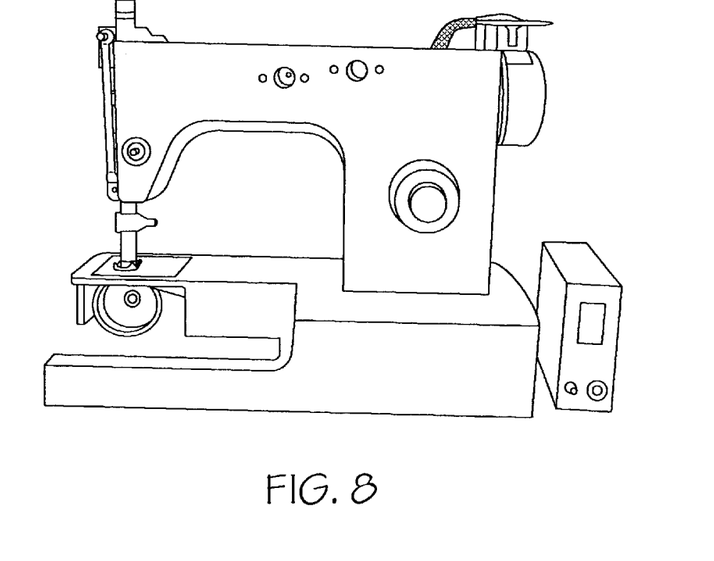
FIG. 8 is a frontal view of the sewing machine platform

Referring to FIG. 8, a modified version of a sewing machine is used to serve as the punching module, holding module, and feed module of the device. The material used in this example was paper. The paper is manually fed into the punching region of the sewing machine. The sewing machine runs at 600 RPM, which means that the machine makes 600 punches per minute, or 10 punches per second. For this example one cycle is equivalent to one punch. The paper is held in place by the clamp of the sewing machine and fed into the punching region by the rotating feed mechanism within the base of the sewing machine, shown in FIG. 9.

Figure 9A:
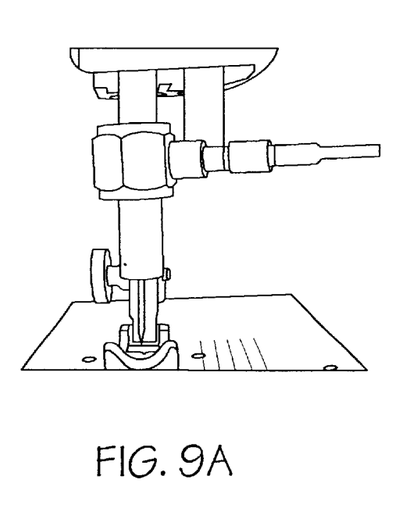
FIG. 9 is a frontal view and a side view of the clamp and punching instrument.
Figure 9B:
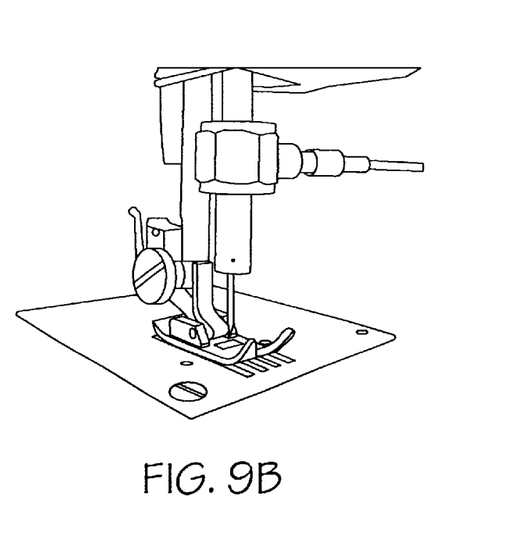
Figure 10:
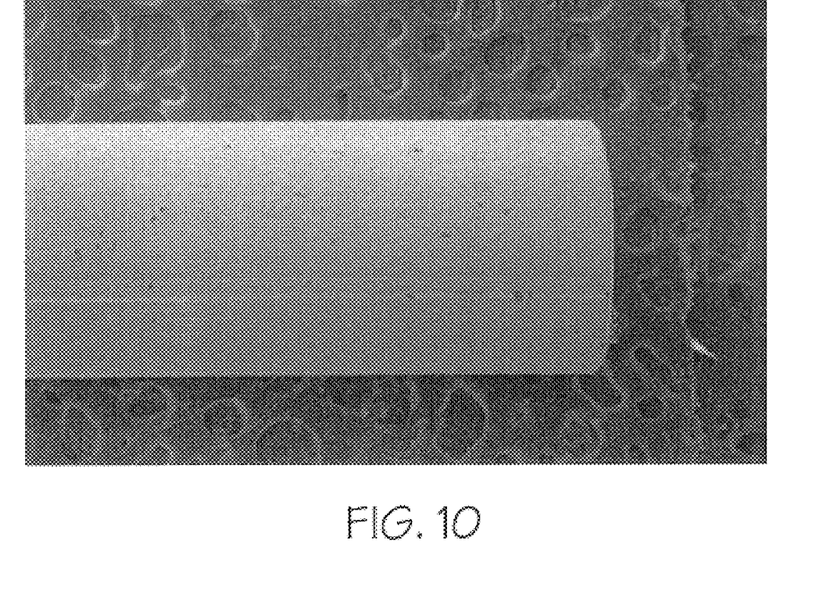
FIG. 10 is a view of flat tipped punches.
Figure 11:
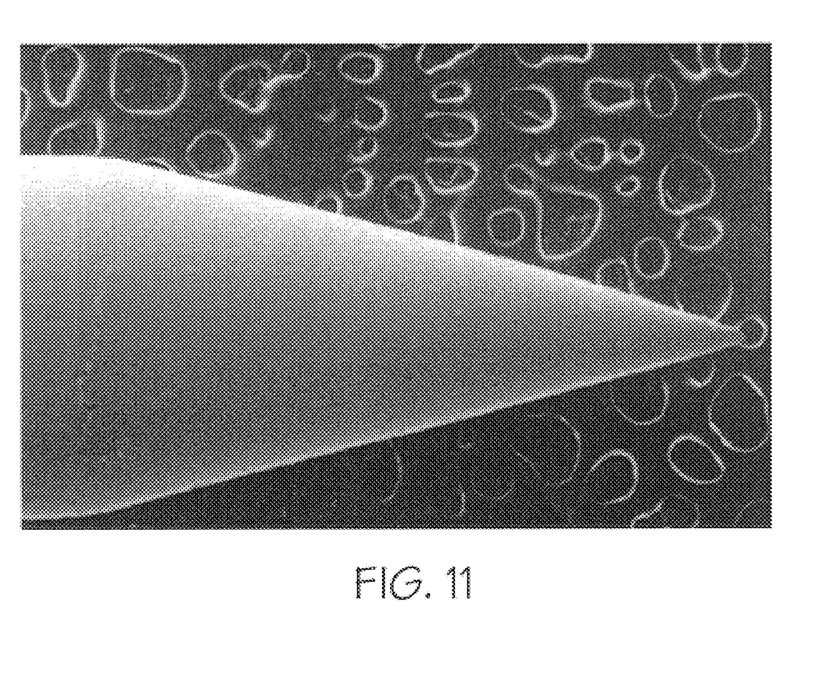
FIG. 11 is a view of pointed, 30° angle punches.

As shown in FIG. 9, the punching module of the modified sewing machine is a needle that was inserted into a punch holder and clamped in place with a setscrew which serves as the punching instrument, the motor of the sewing machine which serves as the driving mechanism to operate the needle. Brass escutcheon pins of 1.24 mm and 1.64 mm in diameter were used as the punching instrument. Some of the punching instruments were blunt and some were pointed. FIG. 10 shows blunt, or flat, tipped punching instruments that were made by cutting a 1.24 mm diameter needle with a diamond wafering blade. FIG. 11 shows conical tipped, or pointed, punching instruments that were made by machining 1.64 mm diameter needles with a 30° included angle.

The load cell of the measuring system was mounted axially on the reciprocating shaft of the sewing machine in line with the holding module. The load cell was a piezoelectric device with 10 lbs capacity and an output of 0.5 V/lb. The sensitivity of the load cell was 0.02% of full scale. The load cell measured the compressive force on the needle and sent a signal to an amplifier. During a typical punching cycle, the needle was driven through the paper as the shaft of the sewing machine moved down, and pulled out of the punched hole as the shaft moved up. The output of the load cell was positive when a compressive force was applied as the punching needle punched through the paper. A tensile force occurred when the punching needle was retracting from the paper, which resulted in a negative voltage output. The signal of the load cell was first sent to an amplifier and then to a data acquisition board (Data Translation DT-301) mounted in a microcomputer for conversion to a digital signal, and then recorded by the data storage instrument and analyzed by the data analysis instrument. The data storage instrument and data analysis instrument were mounted in the same microcomputer as the data acquisition board.

Figure 12:
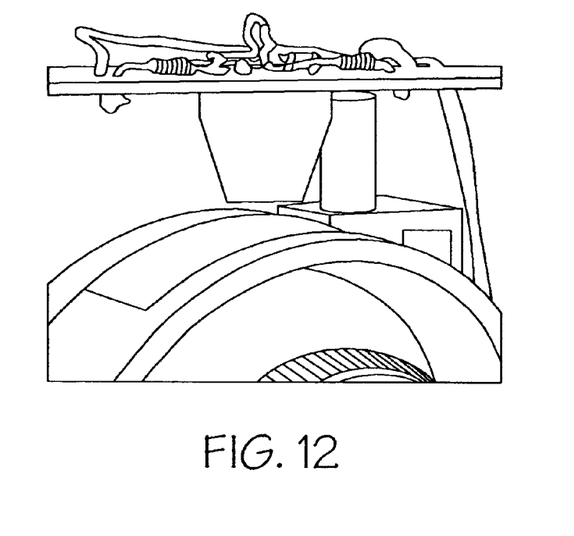
FIG. 12 a frontal view of the sensor mechanism.

A sensor mechanism, shown in FIG. 12, was used to limit the data collected to only that portion of the cycle when the paper was being penetrated, when the force was compressive. A piece of tape was attached to the flywheel of the sewing machine. The length of the tape represented the part of the cycle where the actual punching was taking place and only represented the compressive component of the force. The sensor was an infrared detector that sensed the tape on the flywheel. When the sensor sensed the tape on the flywheel, it sent a signal, after an analog to digital conversion in the data acquisition board, to the microcomputer, thereby alerting the microcomputer that compressive force was being used against the paper. The microcomputer recorded data for the compressive force portion of the cycle.

The microcomputer continued to record the compressive force used against the material for a series of punches. A commercial computer software package Microsoft Excel was used to graph the peak punching force (the greatest compressive force value obtained for each punch) as it changed with the number of punches. Using the capability of Microsoft Excel, a trend line for the variation of peak punching force with the number of punches, and the equation to the trend line were obtained. The slope of the trend line was used as a measure of the abrasiveness of the paper.

Many different types of paper were selected for testing based on the paper's thickness, surface finish, and the availability and manufacturing process involved in making these papers. The papers included: print/copying paper, recycled newspaper, glazed paper, coated and uncoated label stock papers, and emery paper. The papers are summarized in Table 1.

TABLE 1

Standard Papers

| Paper Type | Paper Thickness (mm) |
|---|---|
| Print/Copying Paper | 0.097 |
| Recycled Newspaper | 0.069 |
| Coated Label Stock | 0.100 |
| Uncoated Label Stock | 0.079 |
| Glazed Paper (Time magazine) | 0.046 |
| 600 Grit Emery Paper | 0.280 |

The print/copying paper was manufactured under controlled conditions, and represents a lower limit of paper abrasiveness. Newsprint and other papers with post consumer content generally include a considerable amount of recycled material, and also contain particles other than the paper matrix and fillers. Glazed paper has a glossy surface finish. These papers were calendared, which gives them a smooth surface. Uncoated label stock and coated label stock are used to make adhesive labels used for price tags and other labels. The uncoated label stock was white, while the coated paper had a specially prepared orange pigment applied to one side. Emery paper is used for grinding surfaces of metals and other materials, and is heavily coated with abrasive particles. Emery paper was used to validate the testing method and to make sure that the test results were consistent with the various papers being used. A 600 grit emery paper was used for testing.

Initial testing with flat-tipped punching needles and conical punching needles of 10° and 30° included angles showed that the tips of the 10° punching needles bent easily under the force required to punch paper. This resulted in inconsistent variations in punching force. The results presented below are restricted to flat punching needles and to sharp punching needles with a 30° angle.

Twenty-five tests were conducted; each test consisted of 1500 punches. The results of sharp punching needle tests show that the magnitude of the force required to punch through the paper generally decreased with increasing number of punches. The print/copying paper and the recycled newspaper have a peak punching force that decreased slightly in magnitude with the progression of the tests. The results of the uncoated label stock, coated label stock, and the glazed papers show a peak punching force which decreased in magnitude with the progression of the test, i.e., the slopes of the trend-lines are negative. The decrease in magnitude noticed for the uncoated label stock, coated label stock, and the glazed papers was greater than the decrease in the magnitude noticed for the print/copying paper and the recycled newspaper. The results for 600-grit emery paper show initially a rapid change in force, but the magnitude of the slope decreased with increasing number of punches. The results of the sharp punching needle tests using the sewing machine platform are summarized in Table 2. The results in Table 2 show that the various papers tested can be ranked on their relative abrasivity based on the slope.

TABLE 2

Sharp Needle Tests with the Sewing Machine Platform

| Paper Type | Paper thickness (mm) | Slope (g/punch) | Intercept (g) |
|---|---|---|---|
| Print/Copying Paper | 0.097 | −0.0021 | 218.2 |
| Recycled Newspaper | 0.069 | −0.0043 | 118.4 |
| Uncoated Label Stock | 0.079 | −0.0040 | 177.8 |
| Coated Label Stock | 0.100 | −0.0207 | 207.4 |
| Glossy Paper (Time magazine) | 0.046 | −0.0165 | 114.8 |
| 600 Grit Emery Paper (1500 points) | 0.280 | −0.0247 | 533.2 |
| (500 point) | | −0.1895 | 576.5 |

The results of the flat needle tests are taken from the average of 25 tests. For the print/copying paper and the recycled newspaper show a peak punching force that decreased slightly in magnitude with the progression of the test. For the uncoated label stock, coated label stock and the glazed papers, the results include the average of eight tests on each paper sample. The results are similar to those for the print/copying paper and the recycled newspaper in that a peak punching force is present that decreased slightly in magnitude with the progression of the test. However, the decrease in magnitude is slightly greater for the uncoated label stock, coated label stock, and glazed papers than the decrease noticed for the print/copying paper and the recycled newspaper. There was difficulty in punching the 600 grit emery paper with a flat needle, therefore, results could not be presented. Results of flat punching needle tests using the sewing machine platform embodiment are summarized in Table 3.

TABLE 3

Flat Needle Tests with the Sewing Machine Platform

| Paper Type | Paper thickness (mm) | Slope (g/punch) | Intercept (g) |
|---|---|---|---|
| Print/Copying Paper | 0.097 | −0.0138 | 683.88 |
| Recycled Newspaper | 0.069 | −0.0182 | 335.94 |
| Uncoated Label Stock | 0.079 | −0.0256 | 532.67 |
| Coated Label Stock | 0.100 | −0.0263 | 603.19 |
| Glossy Paper (Time magazine) | 0.046 | −0.0153 | 352.20 |

The slope in Table 3 can be used to rank the different papers when they are punched with a flat needle. This ranking is different from that obtained when using sharp punching needles. A possible reason for this is that when a sheet was punched with a flat punching needle, a clean hole was not formed. A chad was usually left hanging on to the sheet. There was also a greater tendency for the sheet to tear when a flat punching needle was used.

Data presented indicates that the force required to punch the different types of paper decreases with increasing number of punches. This indicates that it typically becomes easier to penetrate the paper. It is reasonable to expect that when a punching needle wears, its tip would become blunt, and there would be an increase in the magnitude of the force required. However, when a punching needle with a conical tip is used, if the travel of the punching needle causes the paper to slide past the transition from the conical to the cylindrical portion of the punching needle, then there would be some wear of the transition region and also wear of the cylindrical portion. This wear could cause a decrease in diameter of the punching needle, and therefore a decrease in the force magnitude. Whether the force increases or decreases with multiple punches will depend on the relative effects of tip blunting and honing of the punching needle diameter. It is apparent that the honing action is dominant and there is a decrease in the magnitude of the punching force with increasing number of punches, i.e., the slope is negative.

The tests were conducted on multiple sheets of paper in order to investigate the possibility of using fewer punches to achieve the same results. The intercept increases linearly with the number of sheets punched, i.e. the magnitude of the punching force is proportional to the total thickness of the sheets being punched. However, the change in the slope of the force versus number of punches trend-line with number of sheets punched is different for the newspaper and the print paper. The results of multiple sheet tests conducted are summarized in Tables 4 and 5.

TABLE 4

Multiple Sheet Tests for Recycled Newspaper

| Number of Sheets | Intercept (g) | Slope (g/punch) |
|---|---|---|
| 1 | 118.43 | −0.0043 |
| 2 | 206.30 | −0.0055 |
| 3 | 325.42 | −0.0107 |
| 4 | 437.73 | −0.0145 |

TABLE 5

Multiple Sheet Tests For Print/Copying Paper

| Number of Sheets | Intercept (g) | Slope (g/punch) |
|---|---|---|
| 1 | 218.2 | −0.0021 |
| 2 | 399.31 | 0.0250 |
| 3 | 626.71 | 0.0576 |
| 4 | 788.82 | 0.1417 |

When punching single sheets of paper, the trend line for the compressive force as a function of the number of punches has a negative slope, indicating that the wear of the punching needle makes penetrations easier. Though the magnitude of the punching force depends on the thickness of the paper, the slope of the trend line is more indicative of the abrasive characteristics of the paper sample being tested. Generally, fillers, pigments and other additives, whether added intentionally or unintentionally, increase the abrasivity of paper. Among the first group of six papers tested, the print/copying paper was the least abrasive and the emery paper was the most abrasive. The recycled newspaper and the glossy magazine paper, with post-consumer content, were the thinnest, but still they were more abrasive than the print/copying paper. The addition of the pigment coating to the label stock increased the thickness, thus increasing the intercept, and at the same time increased the abrasiveness of the paper.

EXAMPLE 2

Figure 13:
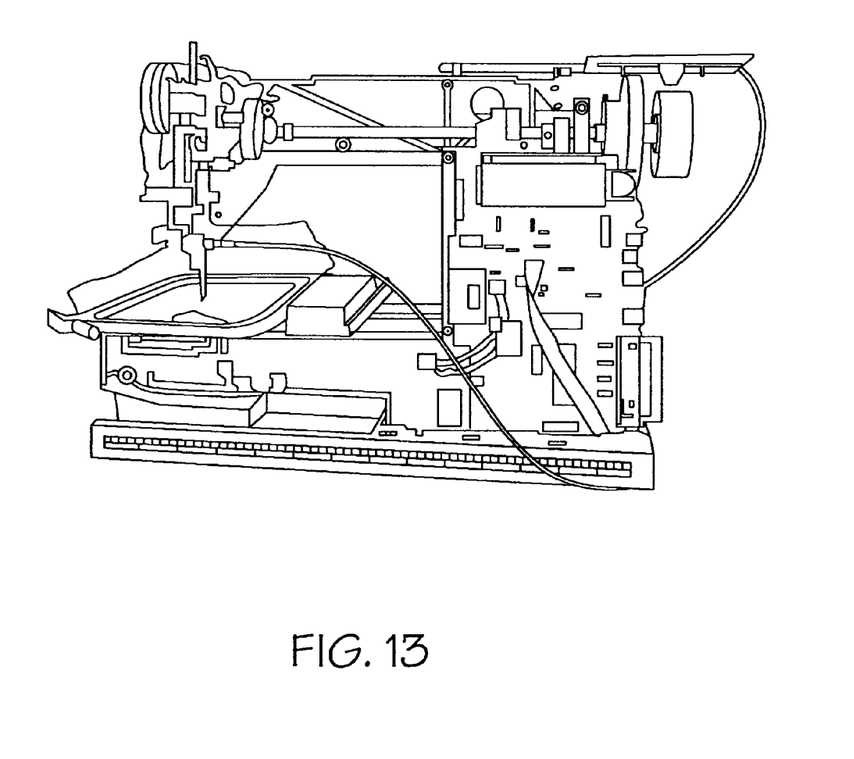
FIG. 13 a frontal view of the embroidery machine platform.

The device used as the testing device for this example is a modified embroidery machine, shown in FIG. 13, which can perform the same functions as the device explained in Example 1. However, this device can also feed the material in various directions, which permits greater automation of the testing procedure. The basic arrangement of the device was the same as explained in Example 1, i.e., paper was used as the material, the punching instrument was a needle, a load cell was mounted on the reciprocating shaft, and the clamping shoe of the machine was used to hold the paper sample in place.

As with Example 1, brass escutcheon pins of 1.24 mm and 1.64 mm in diameter were used. Brass escutcheon pins of 1.24 mm and 1.64 mm in diameter were used as the punching instrument. Some of the piercing instruments were blunt and some were pointed. Blunt, or flat, tipped piercing instruments (shown in FIG. 7) were made by cutting a 1.24 mm diameter pin with a diamond wafering blade. Conical tipped, or pointed, piercing instruments (shown in FIG. 8) were made by machining 1.64 mm diameter pins with a 30° included angle.

The load cell of the measuring system was mounted axially on the reciprocating shaft of the machine in line with the holding module. The load cell was a piezoelectric device with 10 lbs capacity and an output of 0.5 V/lb. The sensitivity of the load cell was 0.02% of full scale. The load cell measured the compressive force and sent a signal to an amplifier. During a typical punching cycle, the pin was driven through the paper as the shaft of the modified embroidery machine moved down, and pulled out of the punched hole as the shaft moved up. The output of the load cell was positive when a compressive force was applied as the punching needle pierces through the paper. A tensile force occurred when the punching needle was retracted from the paper, which resulted in a negative voltage output. The signal of the load cell was first sent to an amplifier and then to a data acquisition board (Data Translation DT-301) mounted in a microcomputer for conversion to a digital signal. The data was then recorded by the data storage instrument and analyzed by the data analysis instrument. The data storage instrument and data analysis instrument were mounted in the same microcomputer as the data acquisition board.

The storing, recording, and analysis of the data were performed in the same manner as described for Example 1. A sensor mechanism, shown in FIG. 12, was used to limit the data collected to only that portion of the cycle when the paper was being penetrated, the compressive force. A piece of tape was attached to the flywheel of the sewing machine. The length of the tape represented the part of the cycle where the actual punching was taking place and only represented the compressive component of the force. The sensor was an infrared detector that senses the tape on the flywheel. When the sensor sensed the tape on the flywheel, it sent a signal, after an analog to digital conversion in the data acquisition board, to the microcomputer, thereby alerting the microcomputer that compressive force was being used against the paper. The microcomputer recorded data for the compressive force portion of the cycle.

One significant difference in this Example as compared with Example 1, is that the paper sample was mounted on the holding and transport module, in this case an embroidery hoop, and the machine was programmed to move the embroidery hoop to punch a rectangular array of holes in the paper. Within the physical size of the embroidery hoop, it was possible to punch roughly 700 holes in a paper sample.

The microcomputer continued to record the compressive force used against the material for a series of punches. A commercial computer software package Microsoft Excel was used to graph the peak punching force (the greatest compressive force value obtained for each punch) as it changed with the number of punches. Using the capability of Microsoft Excel, a trend line for the variation of peak punching force with the number of punches, and the equation to the trend line were obtained. The slope of the trend line was used as a measure of the abrasiveness of the paper.

The paper types explained in Example 1 (Table 1) were also used for this Example, except for the emery paper. In addition, decorative papers were tested. The decorative papers were prepared using different paper making parameters including flocculation, calendaring ash content basis weight, and thickness.

Testing using Example-1 showed that the 10° included angles for the conical punches resulted in the tips being bent under the action of the punching force, resulting in inconsistent variations of the punching force. The results presented below are restricted to flat punching needles and to sharp punching needles with a 30° angle.

TABLE 6

Sharp Needle Tests with the Embroidery Machine Platform

| Paper Type | Paper thickness (mm) | Slope (g/punch) | Intercept (g) |
| --- | --- | --- | --- |
| Print/Copying Paper | 0.097 | −0.0132 | 272.28 |
| Recycled Newspaper | 0.069 | −0.0217 | 159.43 |
| Uncoated Label Stock | 0.079 | −0.0188 | 229.83 |
| Coated Label Stock | 0.100 | −0.0568 | 241.02 |
| Glossy Paper (Time magazine) | 0.046 | −0.0226 | 153.33 |

The results of the sharp punching needle tests show in a peak punching force magnitude that decreased slightly with the progression of the test on the print/copying paper, recycled newspaper, and uncoated label stock. The results of the coated label stock and the glossy paper show a peak punching force magnitude that decreased with the progression of the test. The decrease in magnitude is slightly greater for the coated label stock and the glossy paper than the decrease in magnitude for the other papers. All of these tests using the embroidery machine platform embodiment are for 700 punches, and averaged for ten tests on each paper type. The results are summarized in Table 6.

TABLE 7

Flat Needle Tests with the Embroidery Machine Platform

| Paper Type | Paper thickness (mm) | Slope (g/punch) | Intercept (g) |
| --- | --- | --- | --- |
| Print/Copying Paper | 0.097 | 0.0197 | 791.91 |
| Recycled Newspaper | 0.069 | −0.0840 | 428.47 |

TABLE 7-continued

Flat Needle Tests with the Embroidery Machine Platform

| Paper Type | Paper thickness (mm) | Slope (g/punch) | Intercept (g) |
| --- | --- | --- | --- |
| Uncoated Label Stock | 0.079 | −0.0214 | 570.22 |
| Coated Label Stock | 0.100 | −0.0231 | 674.77 |
| Glossy Paper (Time magazine) | 0.046 | −0.0294 | 394.39 |

The results of the flat punching needle tests for the print/copying paper show a peak punching force that increased with the progression of the test. The results for the recycled newspaper show a peak punching force that decreased slightly with the progression of the test. The results for the uncoated label stock, coated label stock and the glossy paper show a peak punching force that decreased with the progression of the test. The decrease in magnitude is slightly greater for the uncoated label stock, coated label stock, and the glossy paper than for the decrease noticed for the recycled newspaper. As mentioned earlier, all these tests using the embroidery machine platform embodiment are for 700 punches, and averaged for ten tests on each paper type. The results are summarized in Table 7.

Generally the trend line for the force as a function of the number of punches has a negative slope, indicating that the wear of the punching needle makes penetrations easier. Though the magnitude of the punching force depends on the thickness of the paper, the slope of the trend line is more indicative of the abrasive characteristics of the paper sample being tested. Among the first group of six papers tested, the print/copying paper was the least abrasive and the emery paper was the most abrasive. The recycled newspaper and the glossy magazine paper, with post-consumer content, were the thinnest but still they were more abrasive than the print/copying paper. The addition of the pigment coating to the label stock increased the thickness thus increasing the intercept, and at the same time increased the abrasiveness of the paper. The results for the embroidery machine consistently show a higher magnitude of both intercept and slope than those shown in Example 1.

In addition to the papers used in Example 1, decorative papers were tested using the modified embroidery machine. The decorative papers had different thickness, ash (filler material) types, ash content, flocculation, calendaring, and recycled fiber content. The details of these papers are summarized in Table 8. These properties are briefly described in the following paragraphs.

TABLE 8

Special Decorative Papers

| Name | Ash Content % | Fiber Recycle % | Ash Type | Calendering H/M/none | Flocculation Medium/Light | Thickness mm | Basis Wt. (lbs) |
| --- | --- | --- | --- | --- | --- | --- | --- |
| Shasta White | 32 | — | $TiO_2$ + $SiO_2$ | H | M–L | 0.105 | 50 |
| Antique White | 41 | — | $TiO_2$ | H | L | 0.147 | 74 |
| Brite White | 38 | — | $TiO_2$ | M | M–L | 0.185 | 75 |
| Barrier | 17 | 25 | $TiO_2$ + Clay | N | M | 0.287 | 115 |
| 35-949 | 21 | 10 | $TiO_2$ + $SiO_2$ | N | M | 0.270 | 97 |

TABLE 8-continued

Special Decorative Papers

| Name | Ash Content % | Fiber Recycle % | Ash Type | Calendering H/M/none | Flocculation Medium/Light | Thickness mm | Basis Wt. (lbs) |
|---|---|---|---|---|---|---|---|
| Almond | 35 | — | $TiO_2$ + $Fe_2O_3$ | M | L | 0.150 | 53 |
| Classic White | 39 | — | $TiO_2$ | H | L | 0.128 | 63 |
| 811 White | 39 | — | $TiO_2$ | N | M–L | 0.238 | 90 |
| Barrier # 40 | 32 | 15 | $TiO_2$ + Clay | M | M–L | 0.100 | 40 |
| Ineff White | 32 | — | $TiO_2$ + $SiO_2$ | H | M+ | 0.100 | 50 |
| Sea White | 39 | 5 | $TiO_2$ | M | M and L | 0.157 | 67 |

The ash type is predominantly $TiO_2$ while some papers contain $TiO_2+SiO_2$ or $TiO_2$+Clay or $TiO_2+Fe_2O_3$. These materials are used as fillers to give strength to the paper matrix and also to enhance other properties such as color and wetting properties. These mostly inorganic ash particles were the predominant cause for the abrasiveness of the paper. Increase in the ash content will increase the abrasiveness of the paper, as more abrasive particles will be present in the paper matrix.

The process of binding of the filler material with the fibers of the paper matrix is called flocculation. In a heavily flocculated material, the fillers are attached to fibers whereas a less flocculated material has the filler more uniformly distributed. Flocculation may increase or decease the abrasiveness of the paper depending on the filler (ash) particle size and type (ash type). The extent of flocculation is classified as either medium (M) or light (L).

Calendaring is the surface finish given to a paper to make it smooth. Glazed papers are calendared. The paper, along with additives, was pressed by rollers in a mill to get the glossy surface finish. The extent of calendaring on the papers is designated as Heavy (H) or Medium (M) or None (N) in Table 8.

All results for the decorative papers are for the 400 punches. Though the trend is for the punching force to increase with paper thickness, the relationship is not linear, indicating that the papermaking parameters such as ash type and content, flocculation and calendaring also influence the punching force. The effect of these papermaking parameters is discussed below. The results of the decorative papers are summarized in Table 9.

TABLE 9

Tests on Decorative Papers

| Name | Slope (g/punch) | Intercept (g) |
|---|---|---|
| 35-949 | −0.0922 | 513.61 |
| 811 White | −0.1206 | 355.96 |
| Almond | −0.1755 | 299.80 |
| Antique White | −0.1597 | 295.95 |
| Barrier | −0.1127 | 646.78 |
| Barrier # 40 | −0.1025 | 209.66 |
| Brite White | −0.1429 | 316.14 |
| Classic White | −0.1483 | 270.43 |
| Ineff White | −0.0858 | 295.34 |
| Sea White | −0.1037 | 278.55 |
| Shasta White | −0.1183 | 280.93 |

Increasing the content of abrasive fillers should generally increase the abrasivity of a paper. Table 9 shows that the slopes are relatively higher for papers the papers with higher ash content, namely Antique White, Brite White, Classic White and 811 White. Paper making practice has shown that $TiO_2$ is one of the most abrasive fillers. Table 9 shows that the slope is higher for papers that contain just $TiO_2$ such as Antique White, Brite White, Classic White, Sea White and 811 White, in comparison to papers with $TiO_2+SiO_2$ (35–949, Shasta White and Ineff White) or $TiO_2$+clay (Barrier #40). Calendaring also affects the magnitude of the force required to punch a paper, i.e. the intercept. Consider the papers Sea White and Antique White. Both have the same ash type, almost the same percentage ash content. The Antique White paper is heavily calendared, rendering it a denser paper that is more difficult to penetrate, as indicated by the intercept values in Table 9.

To summarize the results on the decorative papers, the tests among the decorative papers showed that the abrasivity of a paper depended upon the various papermaking parameters, namely the ash type and content, calendaring, and flocculation. Papers that contain larger amounts of $TiO_2$ that are not flocculated but are heavily calendared are likely to be the most abrasive.

Having described the invention in detail and by reference to preferred embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A device for measuring abrasive properties of a material comprising:

a punching module comprising a punching instrument for punching said material, a driving mechanism for operating said punching instrument, and a measurement system that measures the amount of the force required to punch said material;

a feed module for moving said material in relation to said punching module;

a holding module that holds said material while said punching instrument penetrates said material, said holding module having a first position and a second position, said holding module being coupled to said feed module in said second position; and an instrument linked to said punching module that records and analyzes said amount of force to calculate said abrasive properties of said material.

2. A device as claimed in claim 1, wherein said punching instrument is a needle.

3. A device as claimed in claim 1, wherein said punching instrument is blunt.

4. A device as claimed in claim 1, wherein said punching instrument is pointed.

5. A device as claimed in claim 1, wherein said holding module comprises a clamp to hold said material.

6. A device as claimed in claim 1, wherein said feed module is a rotating mechanism that moves said material along said device.

7. A device as claimed in claim 1, wherein said feed module moves said material in a first direction.

8. A device as claimed in claim 1, wherein said feed module moves said material in a second direction.

9. A device as claimed in claim 1, wherein instrument maintains a continuous record of said amount of force required to punch said material.

10. A device as claimed in claim 1, wherein said instrument maintains a continuous record of the unremitted force required to make a series of punches in said material.

11. A device as claimed in claim 1, wherein said measuring system comprises:

a load cell that provides a positive output signal and a negative output according to the force being applied to said load cell; and a sensor mechanism which detects compressive force output of said load cell.

12. A device as claimed in claim 11, wherein said load cell is a force measuring device.

13. A device as claimed in claim 11, wherein said load cell provides said compressive force output when said punching module is punching said material.

14. A device as claimed in claim 11, wherein said load cell provides said tensile force output when said punching module is retracting from said material.

15. A device as claimed in claim 11, wherein said sensor mechanism comprises a movement tracking device linked to said driving mechanism, and a sensor relative to said movement tracking device, wherein said sensor detects the movement of said movement tracking device.

16. A device as claimed in claim 15, wherein said sensor is an infrared optical detector.

17. A device as claimed in claim 1, wherein said material is paper.

18. A device as claimed in claim 1, wherein said material is selected from the group consisting of sheet metal, foil, plastic sheet, plastic foil, woven fabric, and non-woven fabric.

19. A device for measuring abrasive properties of a material comprising:

a punching module comprising a punching instrument for punching said material, a driving mechanism for driving said punching instrument, and a measurement system that measures of the amount of force required to make a punch in said material, wherein said measurement system comprises a load cell that provides a positive output signal and a negative output according to the force being applied to said load cell, and a sensor which detects compressive force output of said load cell;

a feed module for moving said material in relation to said punching module;

a holding module that holds said material while said punching instrument penetrates said material, said holding module having a first position and a second position, said holding module being coupled to said feed module in said second position; and an instrument linked to said punching module, wherein said instrument collects said amount of force placed on said load cell when said sensor detects said compressive force output of said load cell, makes a continuous record of said amount of force and analyzes said record to calculate said abrasive properties of said material.

20. A device for measuring abrasive properties of a material comprising:

a punching module comprising a punching instrument for punching said material, a driving mechanism for driving said punching instrument, and a measurement system that measures the unremitted force required to make a series of punches in said material, wherein said measurement system comprises a load cell that provides a positive output signal and a negative output according to the force being applied to said load cell, and a sensor which detects a compressive force output of said load cell;

a feed module for moving said material in relation to said punching module;

a holding module that holds said material while said punching instrument penetrates said material, said holding module having a first position and a second position, said holding module being coupled to said feed module in said second position; and an instrument linked to said punching module, wherein said instrument collects said unremitted force on said load cell when said sensor detects said compressive force output of said load cell, makes a continuous record of said unremitted force and analyzes said record to calculate said abrasive properties of said material.

21. A method for measuring abrasive properties of a material comprising:

placing said material on a feeding module;

feeding said material relative to a punching module, wherein said punching module comprises a punching instrument for punching said material, a driving mechanism for operating said punching instrument, and a measurement system that measures the amount of force required to punch said material;

holding said material stationary with a holding module;

punching said material with said punching instrument;

measuring the amount of force necessary for said punching instrument to punch said material;

storing said amount of force necessary for said punching instrument to punch said material;

recording said amount of force that is stored;

analyzing said amount of force; and determining the abrasiveness of said material.

22. A method for measuring abrasive properties of a material as claimed in claim 21, wherein said record of said amount of force required to punch said material is a continuous record of said amount of force required to punch said material.

23. A method for measuring abrasive properties of a material as claimed in claim 21, further comprising the steps of repeating the above steps in order to obtain a continuous record of said amount of force needed for said punching instrument to punch said material;

maintaining a continuous record of an unremitted force needed for said punching instrument to make a series of punches in said material;

analyzing said continuous record of said unremitted force needed for said punching instrument to punch said material; and determining the abrasiveness of a material.

24. A method as claimed in claim 21, wherein said punching instrument is a needle.

25. A method as claimed in claim 21, wherein said punching instrument is blunt.

26. A method as claimed in claim 21, wherein said punching instrument is pointed.

27. A method as claimed in claim 21, wherein said holding module comprises a clamp to hold said material.

28. A method as claimed in claim 21, wherein said feed module is a rotating mechanism that moves said material along said device.

29. A method as claimed in claim 21, wherein said feed module moves said material in a first direction.

30. A method as claimed in claim 21, wherein said feed module moves said material in a second direction.

31. A method as claimed in claim 21, further comprising the steps of using a sensor mechanism to sense when compressive force is being used by said punching instrument;

signaling to a computer when said compressive force is being used by said punching instrument; and recording said compressive force received from said load cell.

32. A method as claimed in claim 31, wherein said load cell is a force measuring device.

33. A method as claimed in claim 31, wherein said load cell provides said compressive force output when said punching module is punching said material.

34. A method as claimed in claim 31, wherein said load cell provides a tensile force output when said punching module is retracting from said material.

35. A method as claimed in claim 31, wherein said sensor mechanism comprises a movement tracking device linked to said punching module, and a sensor relative to said movement tracking device, wherein said sensor detects the movement of said movement tracking device.

36. A method as claimed in claim 35, wherein said sensor is an infrared optical detector.

37. A method as claimed in claim 21, wherein said material is paper.

38. A method as claimed in claim 21, wherein said material is selected from the group consisting of sheet metal, foil, plastic sheet, plastic foil, woven fabric, and non-woven fabric.

39. A method for measuring abrasive properties of a material comprising:

feeding said material through a punching module;

positioning said material relative to a punching instrument;

holding said material stationary;

punching said material with said punching instrument;

measuring the amount of force necessary for said punching instrument to punch said material;

storing said amount of force measurement necessary for said punching instrument to punch said material;

recording said amount of force that is stored;

repeating the above steps in order to obtain a continuous record of said amount of force needed for said punching instrument to punch said material;

maintaining a continuous record of said amount of force needed for said punching tool to punch said material;

analyzing said record of said amount of force needed for said punching tool to punch said material; and determining the abrasiveness of a material.

40. A method for measuring abrasive properties of a material comprising:

feeding said material through a punching module;

positioning said material relative to a punching instrument;

holding said material stationary;

punching said material with said punching instrument;

measuring the amount of force necessary for said punching instrument to punch said material;

storing said amount of force necessary for said punching instrument to punch said material;

recording said amount of force necessary for said punching instrument to punch said material;

repeating the above steps in order to obtain a continuous record of an unremitted force needed for said punching instrument to punch said material;

maintaining a record of said unremitted force needed for said punching instrument to punch said material;

analyzing said continuous record of said unremitted force needed for said punching instrument to punch said material; and determining the abrasiveness of a material.

* * * * *

UNITED STATES PATENT AND TRADEMARK OFFICE
CERTIFICATE OF CORRECTION

PATENT NO. : 6,612,150 B2
DATED : September 2, 2003
INVENTOR(S) : Raghavan Srinivasan It is certified that error appears in the above-identified patent and that said Letters Patent is hereby corrected as shown below:

Column 15,
Line 29, reads as, "wherein instrument", should read -- wherein said instrument --.

Signed and Sealed this

Thirteenth Day of July, 2004

JON W. DUDAS
*Acting Director of the United States Patent and Trademark Office*